United States Patent
Murphy

(10) Patent No.: US 9,841,405 B2
(45) Date of Patent: Dec. 12, 2017

(54) METHOD OF CALIBRATING A CONCENTRATION SENSOR

(71) Applicant: SSI Technologies, Inc., Janesville, WI (US)

(72) Inventor: Gregory P. Murphy, Janesville, WI (US)

(73) Assignee: SSI Technologies, Inc., Janesville, WI (US)

( * ) Notice: Subject to any disclaimer, the term of this patent is extended or adjusted under 35 U.S.C. 154(b) by 132 days.

(21) Appl. No.: 14/702,393

(22) Filed: May 1, 2015

(65) Prior Publication Data

US 2016/0320349 A1 Nov. 3, 2016

(51) Int. Cl.
*G01N 29/30* (2006.01)
*G01N 29/024* (2006.01)
*G01N 29/32* (2006.01)

(52) U.S. Cl.
CPC ........... *G01N 29/30* (2013.01); *G01N 29/024* (2013.01); *G01N 29/326* (2013.01); *G01N 2291/011* (2013.01); *G01N 2291/0217* (2013.01); *G01N 2291/045* (2013.01)

(58) Field of Classification Search
CPC ............... G01N 29/30; G01N 29/4463; G01N 2291/011; G01N 2291/045
See application file for complete search history.

(56) References Cited

U.S. PATENT DOCUMENTS

| 6,012,779 A * | 1/2000 | Morris ................. A61B 8/0875 310/336 |
| 7,389,693 B2 * | 6/2008 | Reed .................... G01N 15/088 73/597 |
| 2012/0118059 A1 * | 5/2012 | Reimer ................. F01N 3/2066 73/290 V |
| 2014/0322418 A1 * | 10/2014 | Cowe ...................... A47J 27/10 426/523 |
| 2015/0089996 A1 * | 4/2015 | Reimer .................. G01N 29/02 73/19.03 |

OTHER PUBLICATIONS

International Vocabulary of Metrology—Basic and General Concepts and Associated Terms; JCGM 200:2008.*

* cited by examiner

*Primary Examiner* — Natalie Huls
(74) *Attorney, Agent, or Firm* — Michael Best & Friedrich LLP

(57) ABSTRACT

A method for calibrating an ultrasonic sensor including a transducer, a reflector spaced a known distance from the transducer, and a memory. A water bath is heated to approximately fifty centigrade and the ultrasonic sensor is at least partially submerged in the water bath. When submerged, an ultrasonic wave is transmitted through a portion of the water bath from the transducer. The ultrasonic wave is transmitted toward the reflector and a reflected ultrasonic wave is received back at the transducer. A time of flight of the ultrasonic wave is measured. A calibration coefficient is determined based on the time of flight of the ultrasonic wave and an expected time of flight of the ultrasonic wave. The calibration coefficient is loaded into the memory of the ultrasonic sensor.

22 Claims, 6 Drawing Sheets

METHOD OF CALIBRATING A CONCENTRATION SENSOR

BACKGROUND

Embodiments of the invention relate to methods of calibrating a sensor configured to determine characteristics of a fluid. In particular, embodiments of the invention relate to calibration of sensors for determining a concentration of a diesel exhaust fluid (DEF).

Selective Catalytic Reduction (SCR) is a method of converting diesel oxides of nitrogen (NOx) emissions, by catalytic reaction, into diatomic benign nitrogen gas ($N_2$) and water ($H_2O$). In clean diesel engines, an SCR system delivers near-zero emissions of NOx.

DEF is used to reduce nitrous oxide (NOx) gases in the exhaust of diesel engines. DEF is a mixture of purified water and urea. In a typical SCR system, DEF is stored in a tank of a vehicle and is injected via one or more injectors into the exhaust at a ratio of about 1:50 to the diesel fuel being burned. The injected urea (in the form of a mist) mixes with the exhaust and breaks down NOx in the exhaust into nitrogen, water, and carbon dioxide.

SUMMARY

To ensure proper operation of an SCR system it is important to sense the quality and quantity of the DEF fluid. When contaminants such as diesel fuel, water, and ethylene glycol, mix with the DEF, the ability of the DEF to reduce the NOx in the exhaust is diminished. Contaminated DEF may also cause damage to the NOx reduction system. It is also important that a sufficient amount of DEF be available for use in the SCR system. In or near the tank, one or more sensors are used to sense certain characteristics of the DEF. The sensors may include, but are not limited to: a level sensor for determining a quantity of DEF in the tank; a concentration sensor for determine the quality of DEF in the tank; and a temperature sensor.

In some embodiments, a single sensor measures the level of the DEF, the concentration of the DEF, and the temperature of the DEF. A single sensor provides a cost-effective solution to measuring the characteristics of the DEF. Generally, the sensor uses reflected ultrasonic waves and the temperature of the DEF to determine a speed of sound within the DEF. Since the speed of sound of the DEF is proportional to the concentration and the temperature of the DEF, the sensor can determine the concentration of the DEF by measuring the speed of sound and the temperature of the DEF. Once the speed of sound is determined for the DEF, the sensor may further calculate a height of the DEF within a storage tank based on the speed of sound and a time of flight of a reflected ultrasonic pulse. When the dimensions of the storage tank are known, the height of the DEF may be converted into a measurement of the amount of DEF (e.g., gallons) present in the storage tank.

Calculating the concentration of DEF relies on precise measurements with the ultrasonic sensor. However, manufacturing tolerances in ultrasonic sensors result in slight differences in the construction of the sensor. When used in service, these slight differences can result in variations of measured values taken by the ultrasonic sensor. For example, a first ultrasonic sensor may measure slightly different values of speed of sound of the DEF than a second ultrasonic sensor, due to the slight differences in construction. Differences in the measured speed of sound produce differences in calculated values of concentrations. In practice, the difference in measured values may be minimized by calibrating the ultrasonic sensor in a test solution.

Thus, in one embodiment, the invention provides a method for calibrating an ultrasonic sensor including a transducer, a reflector spaced a known distance from the transducer, and a memory. The method includes, heating a water bath to a predetermined temperature and submerging the ultrasonic sensor, at least partially in the water bath. When submerged, an ultrasonic wave is transmitted through a portion of the water bath from the transducer. The ultrasonic wave is transmitted toward the reflector and a reflected ultrasonic wave is received back at the transducer. A time of flight of the ultrasonic wave is measured. A calibration coefficient is determined based on the time of flight of the ultrasonic wave and an expected time of flight of the ultrasonic wave. The calibration coefficient is then loaded into the memory of the ultrasonic sensor.

It should be observed that embodiments of the invention are applicable to calibration of a variety of ultrasonic sensors and are not limited to ultrasonic sensors used in DEF. The variety of ultrasonic sensors may measure a speed of sound in a variety of fluids, including but not limited to, gasoline fuel, diesel fuel, engine oil, hydraulic fluid, and transmission fluid. Therefore, calibration of the variety of sensors during manufacturing results in increased accuracy of speed of sound measurements and thereby increased accuracy of concentration measurements determined based on the speed of sound measurements.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

It should be noted that a plurality of hardware and software based devices, as well as a plurality of different structural components may be used to implement the invention. In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processors. As such, it should be noted that a plurality of hardware and software based devices, as well as a plurality of different structural components may be utilized to implement the invention. For example, "control units" and "controllers" described in the specification can include one or more processors, one or more memory modules including non-transitory computer-readable medium, one or more input/output interfaces, and various connections (e.g., a system bus) connecting the components.

Embodiments of the invention as described herein are described with respect to calibration of a sensor for DEF used in an SCR system. However, the invention described herein can be applied to, or used in conjunction with a variety of fluids, fuels and oils (e.g., gasoline fuel, diesel fuel, engine oil, hydraulic fluid, transmission fluid, etc.).

Figure 1:
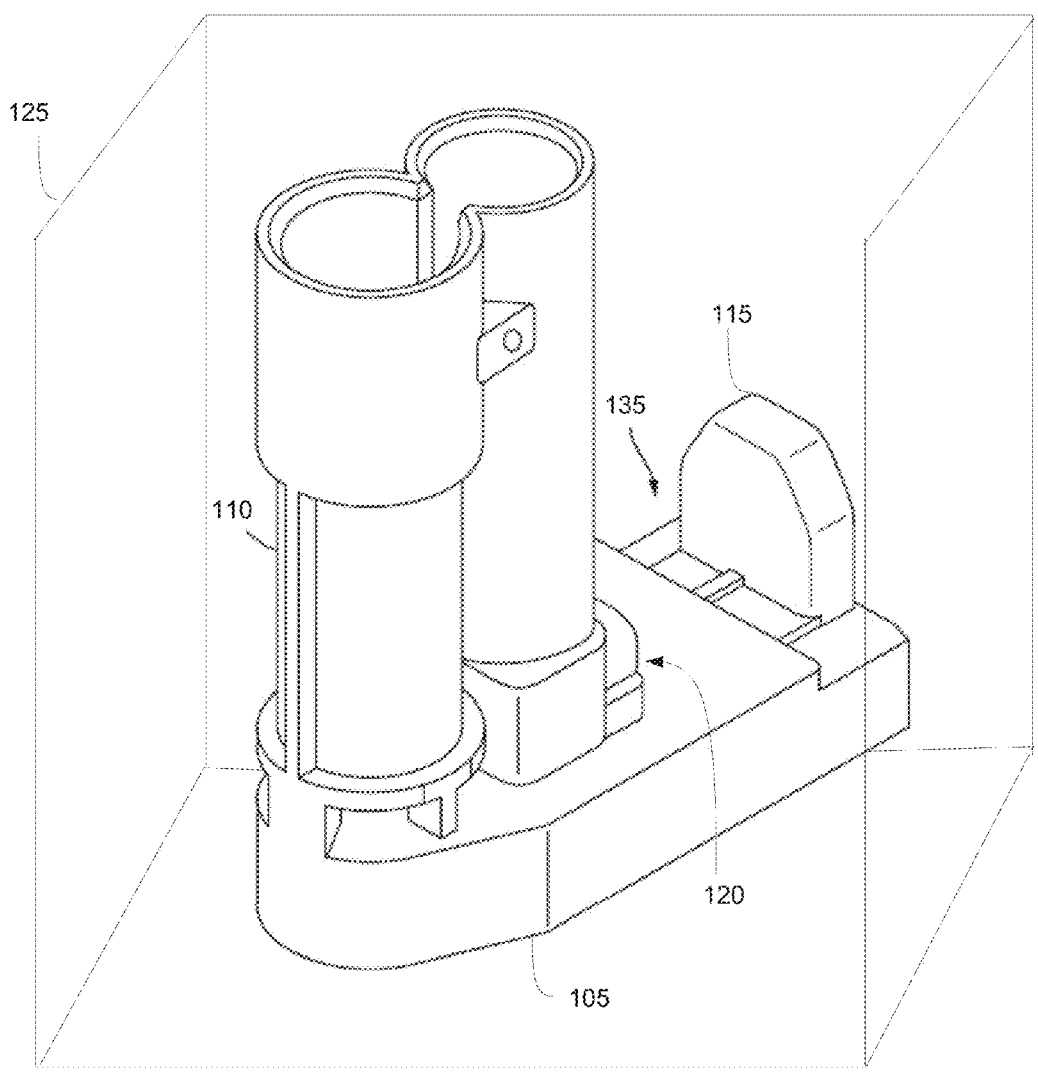
FIG. 1 is a perspective view of an ultrasonic sensor according to one embodiment of the invention.

FIG. 1 illustrates a perspective view of an ultrasonic sensor 100. In the example shown, the ultrasonic sensor 100 includes a base 105, a level focus tube 110, a reflector 115, and a transducer 120 (e.g., a piezoelectric ultrasonic transducer). The ultrasonic sensor 100 is designed to be at least partially submerged in a fluid within a storage tank 125. The transducer relies on the fluid to act as a medium for transmission of ultrasonic waves. As the transmission and reception of ultrasonic waves determine the characteristics of the fluid, the ultrasonic sensor 100 only determines the characteristics of the fluid when the fluid is of sufficient height to cover the transducer 120 and the reflector 115. If the fluid is not covering the transducer 120, the ultrasonic sensor 100 outputs a signal indicative of insufficient fluid in the storage tank 125 to measure (e.g., "empty"). It should be noted that in some embodiments, the reflector 115 may be a separate component external to the ultrasonic sensor. In such an embodiment, the ultrasonic sensor 100 and the reflector 115 are positioned a predetermined distance from each other.

Figure 2:
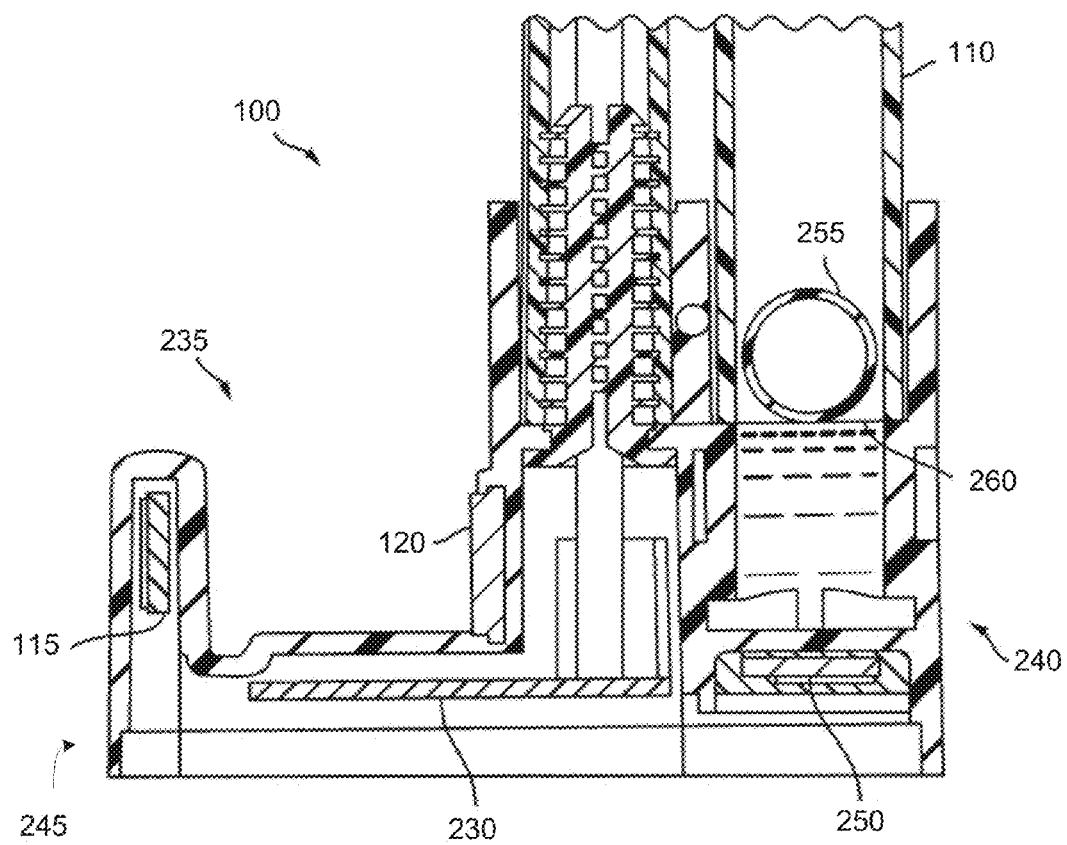
FIG. 2 is a cross-sectional view of the ultrasonic sensor of FIG. 1.

FIG. 2 illustrates a cross-sectional view of the ultrasonic sensor 100. As illustrated, the cross-section is taken along the length of the ultrasonic sensor 100 such that the level focus tube 110, the reflector 115, and the transducer 120 are sliced by a vertical plane. The ultrasonic sensor 100 includes a printed circuit board (PCB 230) and a plurality of sensors. In the illustrated embodiment, the plurality of sensors includes a concentration sensor 135, a level sensor 240, and a temperature sensor 245. In other embodiments, the ultrasonic sensor 100 may include more or less sensors than shown in the illustrated embodiment. Each of the plurality of sensors is electrically coupled to the PCB 230. The PCB 230 includes a control system (FIG. 3), which, among other things, provides power to the plurality of sensors, analyzes data from the plurality of sensors; and outputs the analyzed data to other components such as an external computer.

The concentration sensor 135 measures a concentration, and thus a quality, of the fluid within the storage tank 125. The quality of the fluid may be determined based on a desired level of concentration of the fluid (e.g., 32.5% urea and 67.5% deionized water). The concentration of the fluid may also be indicative of the density of the fluid. Hence, by determining the concentration of the fluid and a temperature of the fluid, the density may also be determined by a known relationship. In addition, impurities in the fluid may be detected by fluid concentration measurements that are outside of a predetermined range. The concentration sensor 135 includes the reflector 115 and the transducer 120. The transducer 120 acts as both a transmitter and receiver of ultrasonic waves. In operation, the transducer 120 transmits an ultrasonic wave through the fluid towards the reflector 115. The ultrasonic wave reflects off of the reflector 115 and propagates back toward the transducer 120. The concentration sensor 135 measures a time of flight of the ultrasonic wave. The ultrasonic sensor 100 uses the control system described below to determine characteristics of fluid within the storage tank 125.

The level sensor 240 determines a level, and thus a quantity, of the fluid within the storage tank 125. In the illustrated embodiment, the level sensor 240 includes a level-sensing transducer (e.g., a piezoelectric ultrasonic transducer) 250 and the level focus tube 110. The transducer 250 acts as both a transmitter and receiver. Some embodiments of the level sensor 240 also include a float 255. In the particular embodiment illustrated, the level sensor 240 includes a float 255 located within the level focus tube 110. Although illustrated as a sphere, the float 255 can be another shape, including, for example, a cylinder. When the level of the fluid is below the top of the level focus tube 110, the float 255 floats on a surface 260 of the fluid contained within the level focus tube 110. The transducer 250 generates an ultrasonic wave, which propagates through the fluid contained within the level focus tube 110. The ultrasonic wave propagates toward the surface 260 of the fluid at the location of the float 255. The ultrasonic wave reflects off of the float 255 and propagates back toward the transducer 250.

In another embodiment, the level sensor 240 does not include a float 255. The transducer 250 generates an ultrasonic wave, which propagates through the fluid contained within the level focus tube 110, toward the surface 260 of the fluid. The ultrasonic wave reflects off of the surface 260 of the fluid and propagates back toward the transducer 250. In both embodiments, with or without the float 255, the transducer 250 sends a signal indicative of the time that the ultrasonic wave was received at the transducer 250. A time of flight of the ultrasonic wave is calculated based on the time difference between when the ultrasonic wave was sent and received.

The temperature sensor 245 determines a temperature of the fluid within the storage tank 125. In one embodiment, the temperature sensor 245 is a thermocouple. In another embodiment, the temperature sensor 245 is a thermistor. In yet another embodiment, the temperature sensor 245 is a resistance temperature sensor. In yet another embodiment, the temperature sensor 245 is an infrared temperature sensor. The temperature sensor 245 outputs a signal indicative of the sensed temperature. In some embodiments, the level sensor 240 and the temperature sensor 245 are combined into a combination sensor capable of sensing both a level and a temperature. In other embodiments, the level sensor 240, the temperature sensor 245, and the concentration sensor 135 are combined into a combination sensor capable of sensing all three parameters.

Figure 3:
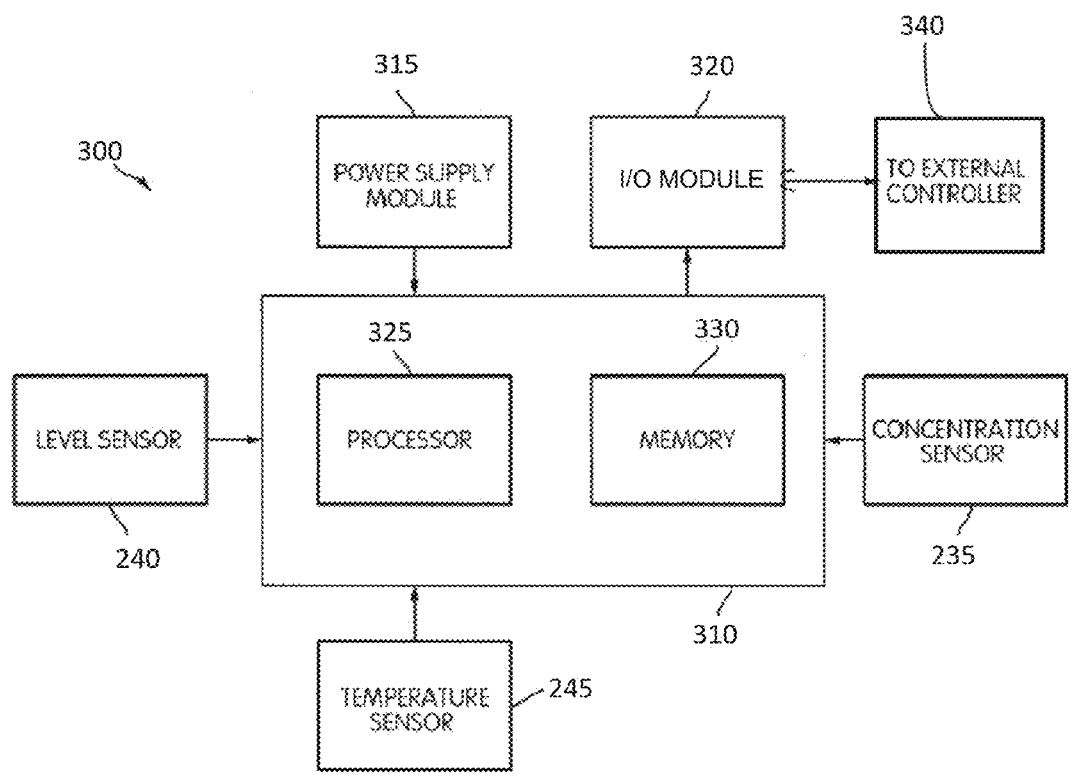
FIG. 3 is a block diagram illustrating a control system of the ultrasonic sensor of FIG. 1.

FIG. 3 illustrates a block diagram of a control system 300 configured to measure the characteristics of the fluid and to calibrate the ultrasonic sensor 100. In some embodiments, the control system 300, apart from the sensors, is mounted on the PCB 230 of the ultrasonic sensor 100. In some embodiments, the control system 300 includes a plurality of electrical and electronic components that provide power, operation control, and protection to the components and modules within the control system 300 and/or the ultrasonic sensor 100. For example, the control system 300 includes, among other things, a controller (such as a programmable microprocessor, microcontroller, or similar device) 310, a power supply module 315, and an input/output module 320.

The controller 310 includes, among other things, a processor 325 and a memory 330. The processor 325 is electrically connected to the memory 330, and executes instructions which are capable of being stored on the memory 330. The controller 310 is configured to retrieve from memory 330 and execute, among other things, instructions related to the control processes and method described herein. In other embodiments, the control system 300 includes additional, fewer, or different components.

The power supply module 315 supplies a nominal voltage to the control system 300 or other components of the ultrasonic sensor 100. In one embodiment, the power supply module 315 supplies a nominal DC voltage. The power supply module 315 is powered by a power source having a nominal voltage and is configured to supply lower voltages to operate circuits and components within the control system 300 or ultrasonic sensor 100.

The input/output module 320 transmits data from the control system 300 to an external controller 340. The input/output module 320 also receives data from the external controller 340. When the ultrasonic sensor 100 is in normal operation, it operates in a measurement mode, in which it transmits data to the external controller 340 indicative of the measured and determined fluid characteristics. The external controller 340 may be, for example, an electronic control unit (ECU) located on a diesel-powered vehicle. The external controller 340 may be linked through a communication module on a vehicle's communication bus (e.g., a CAN bus). In some embodiments, the input/output module 320 communicates by means of a protocol such as J1939 or CAN bus for communicating directly to the external controller 340. In other embodiments, the input/output module 320 communicates under other suitable protocols, including analog or digital signals, depending on the needs of the specific application. In some embodiments, the input/output module 320 communicates by means of a pulse-width modulated signal.

Figure 4:
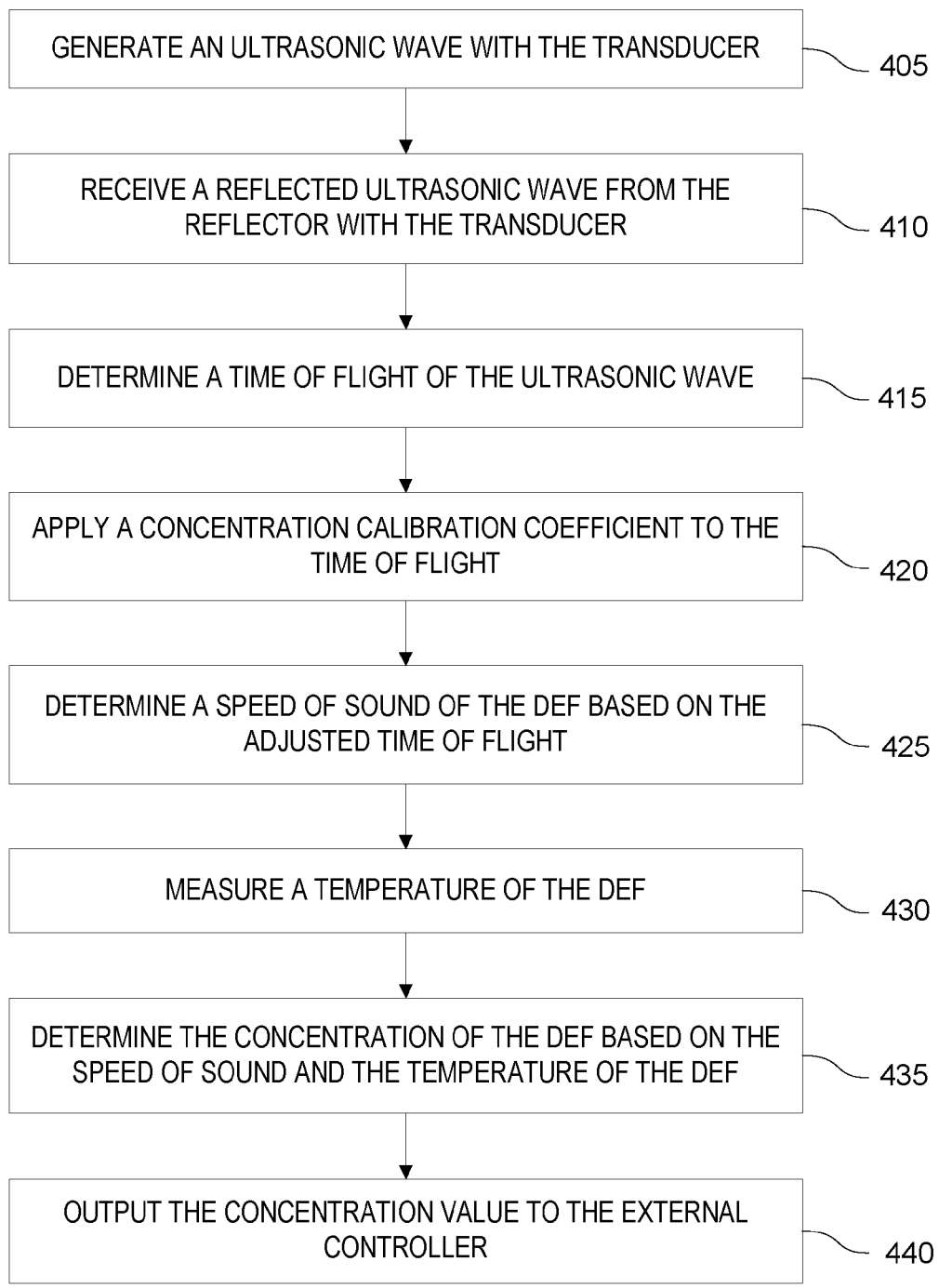
FIG. 4 is a flowchart of a method of performing a measurement with the ultrasonic sensor of FIG. 1.

Illustrated in FIG. 4 is one embodiment of a measurement method 400 by which the ultrasonic sensor 100 determines characteristics (e.g., a concentration) of DEF. The measurement method 400 is performed with the ultrasonic sensor 100 during normal operation (e.g., when submerged in DEF). The transducer 120 transmits an ultrasonic wave directed towards the reflector 115 (step 405). The transducer 120 receives the ultrasonic wave reflected from the reflector 115 (step 410). The controller 310 receives a signal from the transducer 120 that indicates when the ultrasonic wave is received at the transducer 120. Based on the signal, the controller 310 calculates a time of flight of the ultrasonic wave based on a time difference between when the ultrasonic wave was generated and when the reflected ultrasonic wave was received (step 415). The controller 310 adjusts the calculated time of flight with a concentration calibration coefficient as determined by the calibration method illustrated in FIG. 5 (step 420). The controller 310 determines a speed of sound of the DEF based on the adjusted time of flight (step 425). The controller 310 inputs a temperature signal from the temperature sensor 245 indicative of a temperature of the DEF (step 430). Based on the temperature and the adjusted speed of sound of the DEF, the controller 310 determines a concentration of the DEF (step 435). In some embodiments, the concentration of the DEF can be determined from a lookup table stored in the memory 330. Alternatively, the controller 310 may calculate the concentration of the DEF based on the temperature and the speed of sound of the DEF with an algorithm. Lastly, the controller 310 outputs a data signal, via the input/output module 320, to the external controller 340 (e.g., a vehicle's control system) indicative of the determined concentration of the DEF (step 440). Various steps described herein with respect to the measurement method 400 are capable of being executed simultaneously, in parallel, or in an order that differs from the illustrated serial manner of execution. The measurement method 400 may also be capable of being executed using fewer steps than are shown in the illustrated embodiment.

During manufacturing of the ultrasonic sensor 100, the ultrasonic sensor 100 may be calibrated. During calibration, the ultrasonic sensor 100 is connected to an external controller 340. In some embodiments, the external controller 340 for calibration is different that the external controller 340 for normal operation of the ultrasonic sensor 100. The external controller 340 may include a computer configured with software to interface with the ultrasonic sensor 100. The external controller 340 may be connected to the input/output module 320 via a connection cable that plugs into a multi-prong adapter located on the ultrasonic sensor 100. The external controller 340 may be configured to initiate and terminate the calibration mode. The external controller 340 may also receive data from the ultrasonic sensor 100 indicative of measurements made by the concentration sensor 135, the level sensor 240, and the temperature sensor 245.

Figure 5:
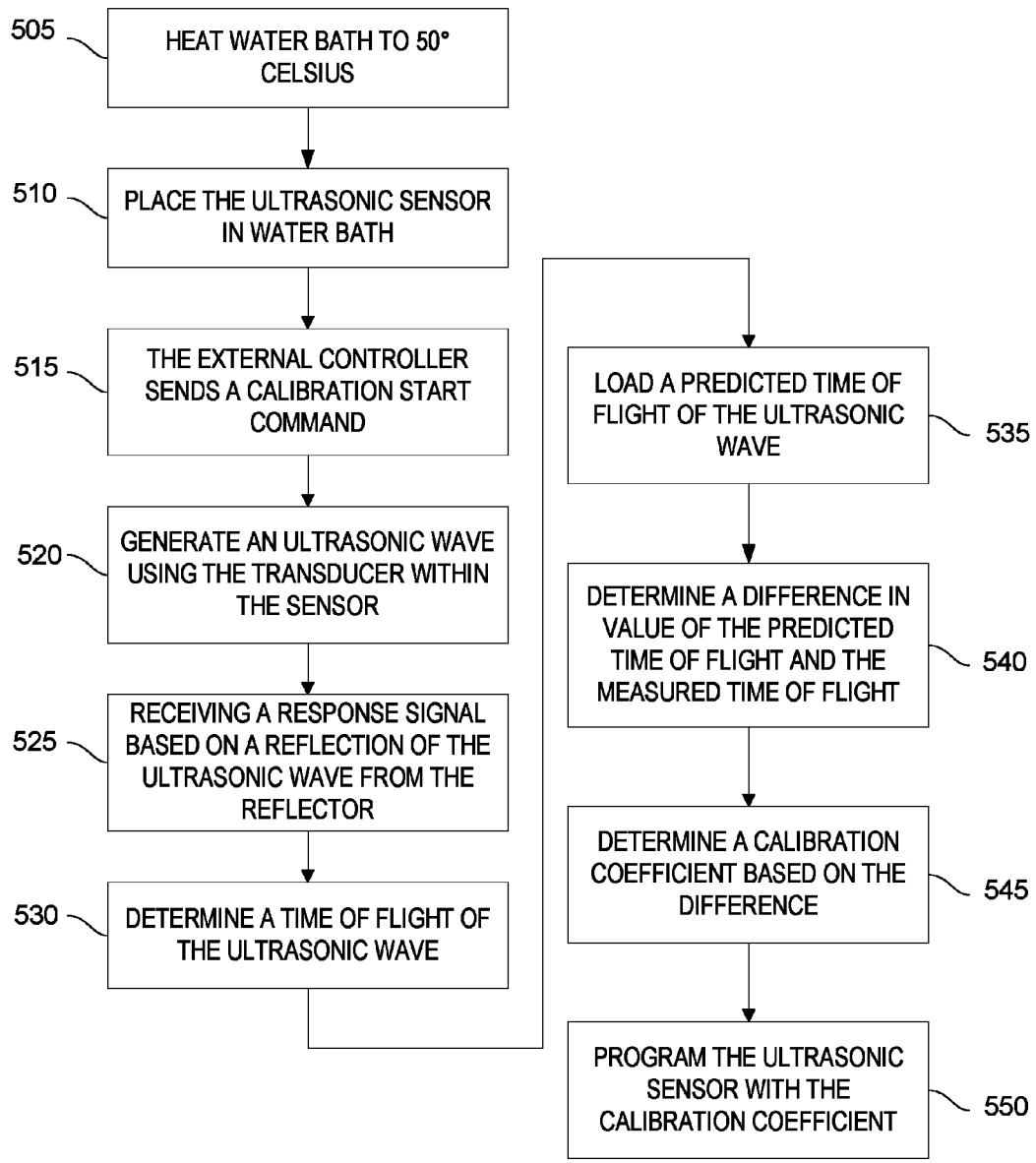
FIG. 5 is a flowchart of a method of calibrating the ultrasonic sensor of FIG. 1.

One embodiment of a calibration method 500 is illustrated in FIG. 5. A water bath is heated to a predetermined temperature (e.g., 30° C., 40° C., 50° C., 60° C., 70° C., 80° C., 90° C., 100° C., etc.). In the embodiment illustrated, the water bath is heated to a predetermined temperature of approximately 50° Centigrade (step 505). The ultrasonic sensor 100 is connected to the external controller 340 via a communication cable or other communication link, and the ultrasonic sensor 100 is at least partially submerged in the water bath (step 510). The external controller 340 sends an initiate message (i.e., a calibration-start command) to the ultrasonic sensor 100 to start calibration (step 515). The controller 310 sends a signal to the transducer (i.e., transducer 120 or transducer 250), and the transducer 120, 250 generates an ultrasonic wave in response to the signal (step 520). The ultrasonic wave is reflected and received back at the transducer 120, 250. In one embodiment, the ultrasonic wave is reflected off of the reflector 115. In another embodiment, the ultrasonic wave is reflected off an external reflector or separate from the ultrasonic sensor 100. In such an embodiment, the external reflector may be temporary, for example, used only during calibration. In either embodiment, the reflector 115 and the external reflector are each spaced a known distance from the transducer 120, 250.

The controller 310 receives a response signal from the transducer 120, 250 indicative of the time that the reflected ultrasonic wave was received (step 525). Based on the time difference between sending the signal to the transducer 120, 250 and receiving the response signal indicative of the reflected ultrasonic wave, the controller 310 determines a time of flight of the ultrasonic wave (step 530). The controller 310 loads a predicted time of flight of the ultrasonic wave from memory 330 (step 535). In one embodiment, the predicted time of flight may be determined in advance of the calibration method 500 based on a standard distance between the transducer 120 and the reflector 115 or between the transducer 250 and the external reflector and a speed of sound of the water bath at the predetermined temperature. The controller 310 compares the predicted time of flight to the measured time of flight, and calculates a difference in value (step 540). The controller 310 determines a calibration coefficient (e.g., a concentration calibration coefficient, a level calibration coefficient, etc.) based on the calculated difference (e.g., setting the calibration coefficient equal to the calculated difference or proportional to the calculated difference) (step 545). The controller 310 loads the calibration coefficient into memory 330 of the ultrasonic sensor 100 (step 550). Similar, to the measurement method 400, various steps described herein with respect to the calibration method 500 are capable of being executed simultaneously, in parallel, or in an order that differs from the illustrated serial manner of execution. The calibration method 500 may also be capable of being executed using fewer steps than are shown in the illustrated embodiment.

It should be noted that the difference between the measured time of flight and the predicted time of flight may arise due to slight differences in the distance between the transducer 120 and the reflector 115 and between the transducer 250 and the external reflector. The slight differences in distance are a natural consequence of the manufacturing process. For example, manufacturing tolerances and variance in the conditions of manufacturing, including machining, molding and assembly processes, can cause slight variations in the actual distance. To achieve greater precision with measurements from the ultrasonic sensor 100 and to achieve greater consistency between each manufactured ultrasonic sensor 100, the calibration component corrects for variations in the distances created during manufacturing.

In another embodiment, the calibration process illustrated in FIG. 5 also includes calibration of the temperature sensor 245. In such an embodiment, the controller 310 receives a sensed temperature of the water bath from the temperature sensor 245, and the controller 310 determines a difference in value between the sensed temperature and the predetermined temperature (e.g., 50° C.) of the water bath. The controller 310 determines a temperature calibration component based on the difference between the sensed temperature and the predetermined temperature (e.g., 50° C.). The controller 310 then loads the temperature calibration component into memory 330. In such an embodiment, in step 545, the controller 310 can determine the predicted time of flight of the ultrasonic wave based on either the sensed temperature along with the temperature calibration coefficient or the predetermined temperature (e.g., 50° C.) of the water bath. In some embodiments, the calibration of the temperature sensor 245 may be performed individually of the calibration method 500.

Additionally, in such an embodiment, the controller 310 may use the temperature calibration coefficient in the measurement method 400. For example, in step 430, after the temperature of the DEF is sensed, the controller 310 adjusts the sensed temperature using the temperature calibration coefficient. Correspondingly, in step 435, the controller 310 determines the concentration of the DEF by referencing a lookup table based on the adjusted temperature and the speed of sound.

By maintaining consistent conditions in the water bath, the consistency of the calibration process increases. It should be noted that in some embodiments, water used in the calibration process is purified water (e.g., deionized or reverse osmosis). Purified water is used for consistency in regard to its physical properties. In addition, maintaining a consistent temperature in the water bath ensures that a speed of sound through the water bath remains relatively constant. Therefore, the calibration method 500 may also include maintaining precise control over the temperature of the water bath. To achieve temperature control, the temperature of the water bath may be held between a lower temperature threshold and an upper temperature threshold by activating a heating element using a temperature sensor and a temperature controller external to the ultrasonic sensor 100.

Figure 6A:
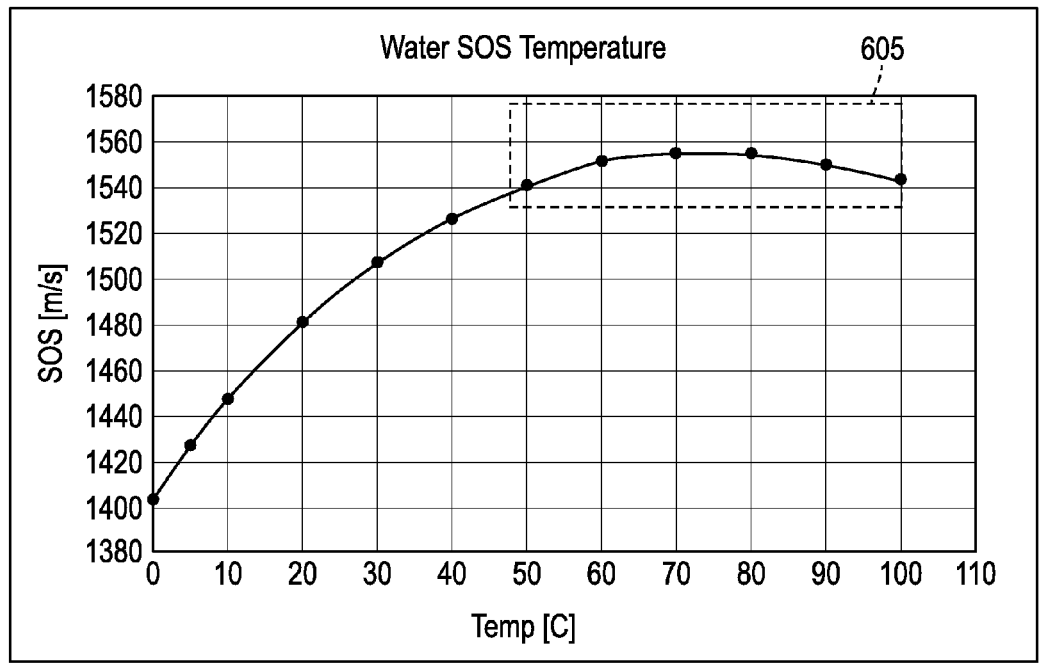
FIGS. 6A and 6B illustrate a graph of a speed of sound of water with respect to a temperature of water and a graph of a derivative of the speed of sound of water with respect to the temperature of water.
Figure 6B:
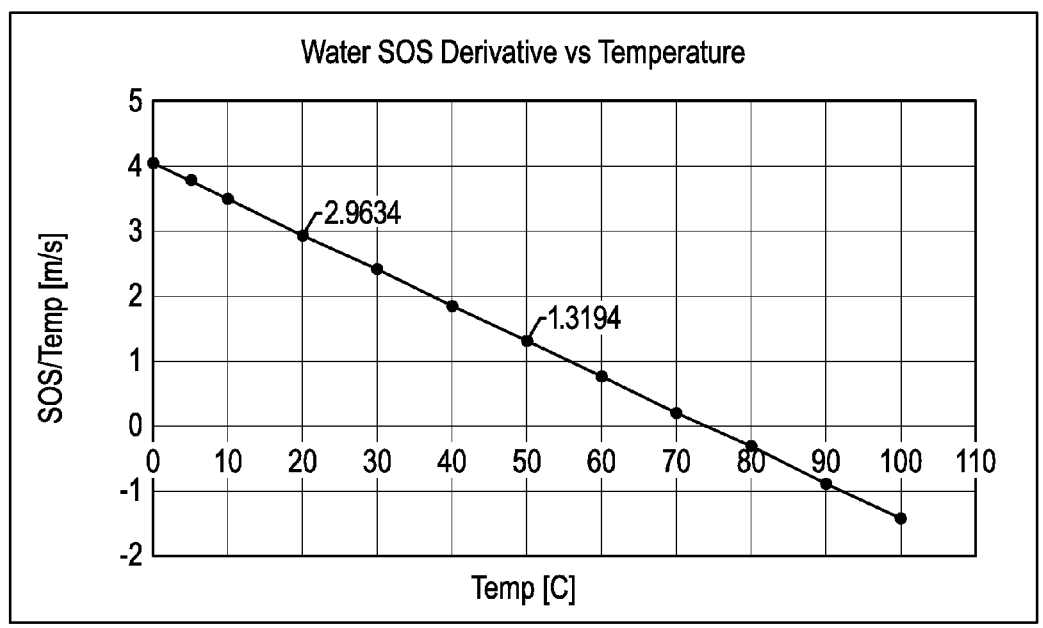

As illustrated in FIG. 6A, the speed of sound of water changes with temperature. As the temperature of the water is increased, the magnitude of the change of the speed of sound is decreased. This property is illustrated by the derivative curve as illustrated in FIG. 6B. As described in the calibration method 500, the temperature of the water bath is raised to 50° C. At around 50° C. and above, the speed of sound does not change significantly during small temperature changes. Therefore, by keeping the temperature of the water bath above 50° C., small fluctuations in temperature of the water bath do not adversely affect the accuracy of calibration. The calibration method 500 is described using a 50° C. water bath due to 50° C. being a safe handling temperature for operators.

However, the calibration method 500 is not limited to 50° C. The calibration process can be performed at other temperatures. To minimize variations in the speed of sound caused from temperature fluctuations, the water bath temperature may be selected to range anywhere in a flat region of the graph of FIG. 6A. For example, a range of 50° C. to 100° C. provides a relatively flat portion 605 of the curve of which variations in the speed of sound can be minimized. In this regard, the water bath temperature may be kept to a temperature where a derivative of the speed of sound with respect to temperature is less than 2. However, at temperatures above about 60° C., other factors may outweigh the benefits of operating at the flat portion 605 of the curve. For example, thermal stress on the ultrasonic sensor 100, safety concerns for operators, and higher energy usage increase as the temperature increases. Therefore, lower water temperatures may be desirable. In that regard, temperatures in a range of 40° C. to 60° C. or a range of 30° C. to 70° C. can provide a relatively flat region of the curve while minimizing these other factors.

Thus, the invention provides, among other things, a method of calibrating an ultrasonic sensor using a hot water bath to achieve consistency in determining calibration coefficients. Various features and advantages of the invention are set forth in the following claims.

What is claimed is:

1. A method for calibrating an ultrasonic sensor including a transducer and a memory, the transducer configured to output an ultrasonic wave, the method comprising:
   heating a water bath to a predetermined temperature, the predetermined temperature being a temperature at which a derivative of a speed of sound with respect to temperature is less than two;
   at least partially submerging the ultrasonic sensor in the water bath;
   transmitting the ultrasonic wave through a portion of the water bath toward a reflector while maintaining the water bath at the predetermined temperature, the reflector spaced a known distance from the ultrasonic sensor;
   receiving the ultrasonic wave reflected off of the reflector;
   measuring a time of flight of the ultrasonic wave;
   comparing the time of flight of the ultrasonic wave to an expected time of flight of the ultrasonic wave;
   determining a calibration coefficient based on the time of flight of the ultrasonic wave and the expected time of flight;
   loading the calibration coefficient into the memory of the ultrasonic sensor.

2. The method of claim 1, wherein the water bath consists of purified water.

3. The method of claim 1, wherein the predetermined temperature is between 30 centigrade and 70 centigrade.

4. The method of claim 1, wherein the predetermined temperature is 50 centigrade.

5. The method of claim 1, wherein heating the water bath to a predetermined temperature further includes:
sensing a temperature of the water bath;
activating a heating element when the temperature of the water bath is equal to a lower temperature threshold; and
deactivating the heating element when the temperature of the water bath is equal to an upper temperature threshold.

6. The method of claim 5, wherein the lower temperature threshold is set to 40 centigrade and the upper temperature threshold is set to 60 centigrade.

7. The method of claim 1, wherein the ultrasonic sensor is configured to determine a concentration of diesel exhaust fluid (DEF).

8. The method of claim 1, wherein calculating the calibration coefficient further includes
calculating a difference of time between the time of flight of the ultrasonic wave and the expected time of flight; and
setting the calibration coefficient proportional to the calculated difference.

9. The method of claim 1, further comprising electrically connecting the ultrasonic sensor to an external controller.

10. The method of claim 9, wherein the ultrasonic sensor is controlled by the external controller.

11. The method of claim 9, wherein calculating the calibration coefficient is performed by the external controller.

12. The method of claim 9, wherein the external controller is communicatively coupled to the ultrasonic sensor via an input/output module.

13. The method of claim 1, further comprising sensing a temperature of the water bath using a temperature sensor of the ultrasonic sensor.

14. The method of claim 13, further comprising determining a temperature calibration coefficient.

15. The method of claim 14, wherein determining the temperature calibration coefficient includes calculating a difference between the sensed temperature and a predetermined temperature.

16. The method of claim 1, wherein the predetermined temperature is between 40 degrees centigrade and 100 degrees centigrade.

17. The method of claim 1, wherein the ultrasonic sensor includes the reflector.

18. The method of claim 1, wherein the ultrasonic sensor is configured to determine, based on the calibration coefficient, at least one selected from the group consisting of a concentration of a fluid, a density of a fluid, and a quality of a fluid.

19. The method of claim 1, wherein the ultrasonic sensor is configured to determine a speed of sound through a fluid based on the calibration coefficient.

20. The method of claim 1, wherein the ultrasonic sensor is configured to determine, based on the calibration coefficient, at least one selected from the group consisting of a level of a fluid and a quantity of a fluid.

21. The method of claim 1, wherein the calibration coefficient is a concentration calibration coefficient.

22. The method of claim 1, wherein the calibration coefficient is a level calibration coefficient.

* * * * *